United States Patent [19]

Bexten et al.

[11] Patent Number: 4,623,490

[45] Date of Patent: Nov. 18, 1986

[54] PROCESS FOR THE PURIFICATION OF SULFONATED ARYL PHOSPHINES

[75] Inventors: Ludger Bexten, Hünxe; Boy Cornils, Dinslaken; Dieter Kupies, Duisburg, all of Fed. Rep. of Germany

[73] Assignee: Ruhrchemie Aktiengesellschaft, Oberhausen, Fed. Rep. of Germany

[21] Appl. No.: 770,303

[22] Filed: Aug. 27, 1985

[30] Foreign Application Priority Data

Aug. 29, 1984 [DE] Fed. Rep. of Germany ....... 3431643

[51] Int. Cl.[4] ............................................ C07C 143/24
[52] U.S. Cl. ............................ 260/505 P; 260/505 R; 260/505 N
[58] Field of Search ............ 260/505 R, 505 P, 505 N

[56] References Cited

U.S. PATENT DOCUMENTS

| | | | |
|---|---|---|---|
| 4,357,280 | 11/1982 | Chylewski | 260/505 |
| 4,483,801 | 11/1984 | Sabot | 260/505 |
| 4,483,802 | 11/1984 | Gartner | 260/505 R |

FOREIGN PATENT DOCUMENTS

| | | | |
|---|---|---|---|
| 3235030 | 3/1984 | Fed. Rep. of Germany. | |
| 0118523 | 1/1981 | Japan | 260/505 |

*Primary Examiner*—Alan Siegel
*Attorney, Agent, or Firm*—Jordan B. Bierman

[57] ABSTRACT

A process for the purification of salts of at least one member of the group consisting of diphenylphosphine-phenyl-m-sulfonic acid, phenylphosphine-di-(m-phenyl-sulfonic acid) and triphenylphosphine-tri-(m-sulfonic acid) from aqueous solutions thereof comprising adding at least a molar equivalent amount of at least one member of the group consisting of di-(n-pentyl)-amine, di-(n-hexyl)-amine and water-soluble salts of said amines to an aqueous solution containing at least one member of the group consisting diphenylphosphine-phenyl-m-sulfonic acid, phenylphosphine-di-(m-phenylsulfonic acid), triphenylphosphine-tri(m-sulfonic acid) and salts thereof to adjust the pH value to $\leq 7$, recovering the precipitate, washing the precipitate and dissolving the same in an aqueous basic solution.

7 Claims, No Drawings

PROCESS FOR THE PURIFICATION OF SULFONATED ARYL PHOSPHINES

STATE OF THE ART

Sulfonated triarylphosphines and their salts are known and the sodium salt of diphenylphosphine phenyl-m-sulfonic acid may be obtained by treating triphenylphosphine with oleum and subsequent neutralization of the reaction mixture with saturated sodium hydroxide solution [Ahrland et al, J. Chem. Soc. (1958), p. 276]. The di- and trisulfonated compounds, phenylphosphine-di(m-phenylsulfonic acid) and triphenylphosphine-tri(m-sulfonic acid) or their salts, can also be recovered by varying the reaction conditions, particularly the reaction period and the reaction temperature as well as the ratio of triphenylphosphine to sulfur trioxide.

Instead of sodium hydroxide, other bases can also be used for the neutralization of the sulfonation mixture. In this manner, for example, the potassium salt and the alkaline earth metal salts can be prepared and precipitated in a crystalline form out of the reaction mixture. When a water-soluble salt such as the sodium salt is treated with a cation exchanger, the free sulfonic acid is formed. Neutralization of the free sulfonic acid with hydroxides or carbonates provides a route for the preparation of further compounds. Lead, zinc, copper, ammonium, quaternary ammonium salts with cations of the formula $N(R_1R_2R_3R_4)^+$ where $R_1$, $R_2$, $R_3$, $R_4$ each denote a straight-chained or branched alkyl of 1 to 4 carbon atoms can thus be formed as aqueous solutions and recovered as solids after evaporation, preferably under reduced pressure.

The salts of sulfonated triarylphosphines find use in various fields of chemical technology. According to GB-PS No. 1,006,261, they are added to photographic emulsions as an agent for preventing hazing. DE-PS No. 2,733,516 describes a process for the telomerization of dienes by reaction of a diene with a compound possessing a mobile hydrogen atom in the presence of a catalyst consisting of a transition metal, in particular palladium or a transition metal compound of the 8th group of the Perodic Table and a water-soluble triarylphosphine of the formula $P(C_6H_4 SO_3M)_n (C_6H_5)_{3-n}$. DE-PS No. 2,700,904 describes the addition of hydrogen cyanide to organic compounds containing at least one ethylenic double bond in the presence of a catalyst system containing a triphenylphosphine sulfonate in addition to a nickel, iron or palladium compound. The process for the preparation of aldehydes by the addition of carbon monoxide and hydrogen to olefins is described in DE-PS No. 2,627,354 which uses water-soluble sulfonated arylphosphines together with rhodium as catalysts.

A disadvantage of the known processes for the preparation of sulfonated aryl phosphines is that numerous byproducts are formed, particularly the various arylphosphines oxides and arylphosphine sulfides. The pure compounds can only be obtained from these mixtures by means of complicated recovery processes which involve high losses.

An improved procedure for the recovery of pure compounds is described in DE-OS No. 3,235,030 in which the sulfonation product is treated with the solution of a water-soluble amine in a water-insoluble solvent. The sulfonated triarylphosphine which is now present in the organic phase is transferred back into the aqueous phase by treatment with an aqueous solution of a base and can then be isolated from said phase. Such a procedure is also suitable for the recovery and purification of sulfonated triphenylphosphine from catalyst systems whose activity has decreased.

The catalyst system containing, among others, sulfonated triphenylphosphines used in the processes listed above as examples are subject to a number of influences which reduce their activity. Thus, iron carbonyl for example, which can form during the reaction owing to the interaction of carbon monoxide with components of the apparatus, acts as a catalyst poison. The sulfonated triphenylphosphines are partly oxidized to inactive phosphine oxides or split off benzene sulfonic acid from other inactive reaction products.

Although it is not difficult to recover sulfonated triphenylphosphines or their salts from the reaction mixture formed during their production or from catalyst systems which have become inactive by the methods described, there is interest in an even simpler process for the separation and purification of these products from aqueous solutions.

OBJECTS OF THE INVENTION

It is an object of the invention to provide a novel process for the selective recovery of sulfonated phenylphosphines so that they do not contain residues of metal catalyst.

This and other objects and advantages of the invention will become obvious from the following detailed description.

THE INVENTION

The novel process of the invention for the purification of salts of at least one member of the group consisting of diphenylphosphine-phenyl-m-sulfonic acid, phenylphosphine-di-(m-phenylsulfonic acid) and triphenylphosphine-tri-(m-sulfonic acid) from aqueous solutions thereof comprises adding at least a molar equivalent amount of at least one member of the group consisting of di-(n-pentyl)-amine, di-(n-hexyl)-amine and water-soluble salts of said amines to an aqueous solution containing at least one member of the group consisting of diphenylphosphinephenyl-m-sulfonic acid, phenylphosphine-di-(m-phenylsulfonic acid), triphenylphosphine-tri-(m-sulfonic acid) and salts thereof to adjust the pH value to $\leq 7$, recovering the precipitate, washing the precipitate and dissolving the same in an aqueous basic solution.

Surprisingly, diphenylphosphine phenyl-m-sulfonic acid, phenylphosphine-di(m-phenyl sulfonic acid) and triphenylphosphine-tri(m-sulfonic acid) form salts with di-(n-pentyl)-amine and di-(n-hexyl)-amine of low solubility in water and in non-polar organic solvents which precipitate in solid form, are easy to filter and can easily be washed out with water. These properties distinctly distinguish them from the salts of other amines. For example, the corresponding sulfonates of di-(n-butyl)amine and tri-(n-butyl)-amine are readily soluble in water and they are therefore not suitable for recovering the above mentioned acids from their aqueous solutions. The sulfonates of di(n-octyl)-amine and tri-(n-octyl)-amine are, on the other hand, of low solubility in water, but readily soluble in non-polar or weakly polar organic solvents and are of oily to syrupy consistency. They dissolve various contaminants, e.g. the amine salts of the sulfonated triphenylphosphine oxides and are therefore unsuitable for the purification of phosphine sulfonic acids and their salts.

According to the invention, di-(n-pentyl)-amine or di-(n-hexyl)-amine are used to separate and purify diphenylphosphine phenyl-m-sulfonic acid, phenylphosphine-di(m-phenylsulfonic acid) and/or triphenylphosphine tri(m-sulfonic acid) and they find use in their pure form, i.e. undiluted by a solvent. Instead of the amines, their water-soluble salts can also act as the precipitating agents. Amine salts are preferably used when higher concentrations of triphenylphosphine sulfonic acid solutions are used or particularly pure precipitates are to be obtained. The higher solubility of amine salts in water compared with the amines simplifies and accelerates the recovery process in such cases. Suitable amine salts are, for example, the halides, acetates and in particular the sulfates and hydrogen sulfates. Amine salts of oxidizing acids such as the nitrates are less suitable because of the possibility of conversion of the phosphines to phosphine oxides.

After the addition of the amine or amine salt, the aqueous phase from which the triphenyl sulfonic acids are precipitated in the form of their salts must have a pH-value not greater than 7 to ensure that the sulfonic acids form the corresponding salts with the amine. To this end, it is necessary that the precipitation with amine occurs from a solution which contains excess acid. Should the aqueous solution not contain excess acid, amine and acid can be added simultaneously or amine can be added first and then acid. It has proved particularly useful to use sulfonic acid for this purpose, but other, preferably non-oxidizing acids such as hydrochloric acid or acetic acid are also suitable. Finally, the neutral or acidic solution can also be reacted with an amine salt.

The amines or amine salts are used in an amount equivalent to or in excess of the triphenyl sulfonic acids and 1.0 to 1.5 times the equivalent amount of amine or amine salt have been successfully employed.

A large excess of precipitating agent can lead to components of the solution other than diphenylphosphine phenyl-m-sulfonic acid, phenylphosphine-di-(m-phenylsulfonic acid) and triphenylphosphine-tri(m-sulfonic acid) being precipitated. They form a viscous to syrupy layer on the solid precipitate of the triphenylphosphine sulfonates which, in contrast to the triphenylophosphine sulfonates, is soluble in organic solvents, particularly in aliphatic and aromatic hydrocarbons or in water and can easily be removed. To increase the solubilizing properties of the hydrocarbons, alcohols of 8 or more carbon atoms such as 2-ethylhexanol can be added. Alcohols of 3 to 6 carbon atoms dissolve the di(n-pentyl)-amine and di-(n-hexyl)-amine salts of the triphenylphosphine sulfonic acids and are therefore not suitable for adding to the hydrocarbons.

The novel process is useful for separating and purifying diphenylphosphine phenyl-m-sulfonic acid, phenylphosphine di(m-phenylsulfonic acid) and triphenylphospine-tri(m-sulfonic acid) present in aqueous solution. From solutions in which two or all three of the compounds are present, the compounds are precipitated out together with di-(n-pentyl)-amine and di-(n-hexy)-amine or their salts. As the mixture of 2 or 3 sulfonic acids can be used for many applications, e.g. as a catalyst component, separation into the mono-,di- and trisulfonic acids is not necessary.

Thus the solutions formed during the sulfonation of triphenylphosphine containing diphenylphosphine phenyl-m-sulfonic acid, phenylphosphine-di(m-phenyl sulfonic acid) and triphenylphosphine-tri(m-sulfonic acid) can be used directly i.e. without prior purification steps. It is merely necessary to dilute them with water to lower the concentration of sulfuric acid and this can extend over a wide range but values of between about 20 and about 50% by weight, based on the solution, have proved to be appropriate.

According to the novel process, the sulfonic acids can also be precipitated without difficulty and in pure form from inactive aqueous catalyst solutions which contain diphenylphosphine phenyl)m-sulfonic acid, phenylphosphine-di(m-phenylsulfonic acid) and/or triphenylphosphine-tri(m-sulfonic acid) in the form of their salts in addition to metal components. To this end, the organic and aqueous solutions have to be separated from one another and the aqueous phase containing sulfonic acid can be used without prior treatment, particularly without prior purification. In must only be ensured that the pH-value is that required for the formation of a precipitate. Thus, if necessary, an acid, preferably sulfuric acid, must be added to the solution. The aqueous phase remaining after separation of the sulfonic acids still contains the dissolved metal component of the catalyst system and can be further treated to recover it. The novel process has proved successful for working up aqueous catalyst solutions which are formed during the telomerization of dienes, the addition of hydrogen cyanide to ethylenically unsaturated compounds and the reaction of olefins with carbon monoxide and hydrogen (hydroformylation). Apart from the sulfonic acids, the aqueous solutions can contain other dissolved components, particularly the phosphine oxides and phosphine sulfides formed from phenylphosphine sulfonic acids by further reaction and benzene sulfonic acid formed by the splitting of the phosphorus-carbon bond as well as salts, which, for example, form during the partial neutralization of the sulfonation mixtures as well as metal complex compounds which are present in the catalyst solutions.

The concentration of the triphenylphosphine sulfonic acids in the aqueous solution is not a critical factor in the feasibility of the process of the invention. Said acids can be separated with great purity both from solutions of high concentration, e.g. 30% by weight (based on the solution) and of low concentration, e.g 1% by weight (based on the solution). It has proved particularly successful to work with solutions whose triphenylphosphine sulfonic acid concentration is 2 to 15% by weight.

The practical implementation of the method of the invention is simple as the amine or the amine salt solution is added gradually to the aqueous solution of the sulfonic acids while stirring at room temperature or with cooling to $-10°$ to $+10°$ C. The amine salts of the triphenylphosphine sulfonic acids precipitate out as waxy to solid precipitates and can be filtered off. To purify them, they are washed or kneaded with water and, if necessary, with an organic solvent as described above.

By treatment with the aqueous solution of a base such as sodium hydroxide or potassium hydroxide, solutions of the corresponding water-soluble salts can be recovered from the di-(n-pentyl)amine or the di-(n-hexyl)amine salt of the diphenylphosphine phenyl-m-sulfonic acid, the phenylphospine-di(m-phenylsulfonic acid) or the triphenyl-tri(m-sulfonic acid). Due to the lower solubility of the diphenylphosphine phenyl-m-sulfonates in water, the treatment is carried out at elevated temperatures of 40° to 80° C. or in greater dilution when this sulfonic acid is present. During this reaction, the amines separate out on the surface of the water as a layer immiscible with water and after separation from the aqueous phase, they can be reused in the process of the invention.

The aqueous solution of the pure triphenylphosphine sulfonates can in many cases be further used as such or be used for the preparation of solutions of other salts or the free acid by using an ion exchanger. Finally, the crystallized salts can be recovered from the solution by evaporation.

In the following examples there are described several preferred embodiments to illustrate the invention. However, it should be understood that the invention is not intended to be limited to the specific embodiments.

The following abbreviations are used in the examples:
TPPTS: Triphenylphosphine-tri-(sodium sulfonate)
TPPOTS: Triphenylphosphineoxide-tri-(sodium sulfonate)
TPPSTS: Triphenylphosphinesulfid-tri-(sodium sulfonate)
TPPDS: Triphenylphosphine-di-(sodium sulfonate)
TPPODS: Triphenylphosphineoxid-di-(sodium sulfonate)
TPPSDS: Triphenylphosphinesulfid-di-(sodium sulfonate)
TPPMS: Triphenylphosphine-mono-(sodium sulfonate)
TPPOMS: Triphenylphosphineoxid-mono-(sodium sulfonate)
BSNS: Sodium benzenesulfonate

EXAMPLE 1

The sulfonation mixture formed during the reaction of triphenylphosphine with 20% oleum was diluted with water to a sulfuric acid concentration of 30.2% by weight and it had the following composition: (Concentration of sulfonic acids calculated as sodium salts)

|         | % by wt. | mMol/1000 g |
|---------|----------|-------------|
| TPPTS   | 2.61     | 46.0        |
| TPPOTS  | 0.73     | 12.5        |
| TPPSTS  | 0.11     | 1.8         |
| TPPDS   | 1.02     | 21.9        |
| TPPODS  | 0.16     | 3.3         |
| TPPSDS  | 0.04     | 0.8         |
| other components | 0.49 |        |

1000 g of this reaction mixture were mixed with stirring with 36 g of di-(n-pentyl)-amine over a period of 30 minutes and stirring was continued for another 30 minutes. The precipitate was filtered off and was washed with 333 g of water. The precipitate was subsequently dissolved by the addition of sufficient 2N aqueous sodium hydroxide for the solution to attain a pH value of 11.5 and the composition of the solution is shown in the following Table. The di-(n-pentyl)-amine released can be recovered from the aqueous phase and reused for precipitation without further purification.

EXAMPLE 2

1000 g of the reaction mixture of Example 1 were mixed with stirring with a solution of 30 g of di-(n-pentyl)-amine in 140 g of aqueous 10% sulfuric acid for a period of 30 minutes and after a further 30 minutes of stirring, the precipitate was worked up as described in Example 1 and the result of this experiment is shown in Table I.

EXAMPLE 3

1000 g of the reaction mixture of Example 1 were mixed with stirring with a solution of 36 g of di-(n-pentyl)-amine in 168 g of aqueous 10% sulfuric acid for a period of 30 minutes and the result of this experiment is shown in Table I.

EXAMPLE 4

1000 g of the reaction mixture of Example 1 were placed in a three-necked flask fitted with a glass filter and a tap at the bottom and were mixed with stirring with a solution of 36 g of di-(n-pentyl)-amine in 168 g of aqueous 10% sulfuric acid over a period of 30 minutes. After a further 30 minutes of stirring, the filtrate was drawn off at the bottom of the flask and the precipitate was stirred twice with 333 g of deionized water, each time for 10 minutes, and was filtered off from the wash water. The precipitate was then dissolved with stirring by the addition of 2N aqueous sodium hydroxide until a pH value of 11.5 was attained. The composition of the solution is given in Table I and the di-(n-pentyl)-amine released was recovered from the aqueous phase and was used for precipitation again without further purification.

TABLE I

Precipitation of triphenylphosphine disulfonic acid and triphenylphosphine trisulfonic acid in the form of di-(n-pentyl) amine salts from 30.2% sulfuric acid.

| Expt.-Nr. | 1 | 2 | 3 | 4 |
|---|---|---|---|---|
| Starting materials |   |   |   |   |
| reaction mixture g | 1000 | 1000 | 1000 | 1000 |
| di-(n-pentyl)amine g | 36 | 30 | 36 | 36 |
| 10% sulfuric acid g | — | 140 | 168 | 168 |
| Ratio |   |   |   |   |
| TPPDS + TPPTS/amine equiv./mol | 1:1.3 | 1:1.1 | 1:1.3 | 1:1.3 |

| products | precipitate | spent acid | precipitate | spent acid and wash water | precipitate | spent acid and wash water | precipitate | wash-water | spent acid |
|---|---|---|---|---|---|---|---|---|---|
| TPPTS g  | 23.15 | 0.60 | 22.29 | 3.57 | 24.18 | 1.88 | 23.84 | 1.60 | 0.24 |
| TPPOTS g | 1.10  | 4.90 | 0.49  | 6.81 | 0.47  | 6.69 | 0.28  | 1.22 | 5.82 |
| TPPSTS g | 0.63  | 0.06 | 0.53  | 0.48 | 0.63  | 0.39 | 0.54  | 0.51 | 0.09 |
| TPPDS g  | 7.15  | 1.71 | 7.88  | 2.24 | 8.89  | 0.66 | 8.82  | 0.40 | 0.78 |
| TPPODS g | 0.45  | 0.81 | 0.29  | 1.29 | 0.30  | 1.23 | 0.10  | 0.54 | 0.93 |
| TPPSDS g | 0.27  | 0.03 | 0.22  | 0.20 | 0.28  | 0.11 | 0.21  | 0.16 | 0.02 |

TABLE I-continued

Precipitation of triphenylphosphine disulfonic acid and triphenylphosphine trisulfonic acid in the form of di-(n-pentyl) amine salts from 30.2% sulfuric acid.

| other components | 0.65 | 3.7 | 0.13 | 4.6 | 0.18 | 4.5 | 0.18 | 0.7 | 3.8 |

EXAMPLE 5

The sulfonation mixture formed during the reaction of triphenylphosphine with 20% oleum at 0° C. was diluted with water to a sulfuric acid concentration of 30% by weight and then was filtered off from unreacted triphenylphosphine. It contained the following sulfonic acids (the sulfonic acids are given in the form of sodium salts)

|  | % by weight | mMol/1000 g |
|---|---|---|
| TPPMS | 3.05 | 83.7 |
| TPPOMS | 0.14 | 3.7 |

2000 g of this reaction mixture were mixed with stirring with a solution of 34 g of di-(n-pentyl)-amine in 160 g of aqueous 10% sulfuric acid (corresponding to 1.3 Mol of amine/Mol of TPPMS) over a period of 30 minutes and stirring was continued for another 30 minutes. The precipitate formed was filtered off and was washed with 1000 g of water. The precipitate was then dissolved at 45° C. by the addition of 1N aqueous sodium hydroxide until the solution had a pH value of 11.5. The di-(n-pentyl)-amine released was recovered from the aqueous phase and used for precipitation again after filtration to remove small amounts of TPPMS. The aqueous sulfonate solution to contain 60.3 g of TPPMS, some of which precipitated as a solid at room temperature, and 1.4 g of TPPOMS. In addition to the sulfuric acid, 0.65 g of TPPMS and 2.3 g of TPPOMS also remained in the wash water and the spent acid.

EXAMPLE 6

1000 g of a spent aqueous catalyst solution containing rhodium and TPPTS were mixed with a solution of 127 g of di-(n-pentyl)-amine in 592 g of aqueous 10% sulfuric acid with stirring and under and inert atmosphere over a period of 30 minutes. Stirring was continued for another 30 minutes and the precipitate was filtered off and was washed with 500 g of water. The filtrate and wash water were combined and analyzed together. The precipitate was dissolved in 107 g of 30% sodium hydroxide solution and 121.8 g of di-(n-pentyl)-amine were recovered which was used again for precipitation without any purification. The TPPTS solution was adjusted to a pH value of 6.5 by the addition of 2.7 g of concentrated sulfuric acid and analyzed. The results are reported in Table II.

TABLE II

Precipitation of triphenylphosphine disulfonic acid and triphenylphosphine-(trisulfonic acid) from a spent aqueous TPPTS/Rh solution

| Starting materials | |
|---|---|
| (a) TPPS/Rh solution, spent | 1000 g |
| di-(n-pentyl)-amine | 127 g |
| subsequently recovered | 121.8 g |
| sulfuric acid, 10% | 592 g |
| (amine/TPPTS + TPPDS 1.05 Mol/equiv.) | |
| deionized water | 500 g |
| (b) sodium hydroxide solution, 30% | 107 g |
| sulfuric acid, concentrated | 2.7 g |

TABLE II-continued

| Results | TPPTS/Rh solution, spent 1000 g | TPPTS solution from precipitation 397 g | filtrate and wash water 1795 g |
|---|---|---|---|
| TPPTS g | 142.4 | 130.6 | 7.50 |
| TPPOTS g | 47.4 | 4.75 | 48.0 |
| TPPSTS g | 7.38 | 4.11 | 3.21 |
| TPPDS g | 4.63 | 4.03 | 0.60 |
| TPPODS g | 10.5 | 0.72 | 10.1 |
| TPPSDS g | 0.67 | 0.53 | |
| BSNS g | 7.36 | 0.38 | 6.79 |
| other components | 44 | 1.4 | 40.0 |
| Rh in % | 100 | 2.7 | 97.0 |
| Fe in % | 100 | 9.0 | 88.2 |

EXAMPLE 7

Example 6 was repeated using di-(n-hexyl)-amine instead of di-(n-pentyl)-amine. The results of this experiment are reported in Table III.

TABLE III

Precipitation of triphenylphosphine disulfonic acid and triphenylphosphine-(trisulfonic acid) from a spent aqueous TPPTS/Rh solution

| Starting materials | |
|---|---|
| (a) TPPTS/Rh solution, spent | 1000 g |
| di-(n-hexyl)-amine | 138 g |
| subsequently recovered | 112 g |
| sulfuric acid, 10% | 546 g |
| (amine/TPPTS + TPPDS 1.10 Mol/equiv.) | |
| deionized water | 1500 g |
| (b) sodium hydroxide solution, 30% | 109 g |
| sulfuric acid, concentrated | 1.7 g |

| Results | TPPTS/Rh solution, spent 1000 g | TPPTS solution from precipitation 591 g | filtrate and wash water 2688 g |
|---|---|---|---|
| TPPTS g | 126.8 | 104.2 | 16.8 |
| TPPOTS g | 51.2 | 6.4 | 49.0 |
| TPPSTS g | 5.2 | 4.2 | 0.6 |
| TPPDS g | 0.7 | 0.6 | |
| TPPODS g | 14.7 | 5.2 | 9.6 |
| TPPSDS g | 0.2 | 0.1 | |
| BSNS g | 6.9 | 3.1 | 3.7 |
| other components | 28 | 8 | 20 |
| Rh in % | 100 | 13.6 | 85.7 |
| Fe in % | 100 | 11.6 | 84.8 |

EXAMPLE 8

This experiment describes the simultaneous precipitation of triphenylphosphine disulfonic acid and triphenylphosphine(trisulfonic acid) and the extraction of rhodium from a spent aqueous catalyst solution such as used in Examples 6 and 7 and the work was carried out in a nitrogen atmosphere. 100 g of aqueous TPPTS/Rh spent catalyst solution, 100 g of toluene and 30 g of 2-ethylhexanol were placed in a glass beaker and mixed with stirring with an aqueous solution of 18.5 g of di-(n-pentyl)-amine in 85 g of aqueous 10% sulfuric acid over a period of 30 minutes. After the mixture had been stirred for another 30 minutes, the precipitate was filtered off in a glass filter funnel and dried in a nitrogen stream. The precipitate was first washed with a mixture of 80 g of toluene and 20 g of 2-ethylhexanol and then with 500 g of water. The filtrate and wash solutions were combined, separated into the water phase and toluene phase and analyzed separately.

The precipitate was dissolved in 80 g of 1N aqueous sodium hydroxide solution and the amine/toluene phase formed was separated off. The aqueous solution was adjusted to a pH value of 6.5 by the addition of 1.3 g of sulfuric acid and analyzed. The results are reported in Table IV.

TABLE IV

Simultaneous precipitation of triphenylphosphine disulfonic acid and triphenylphosphine (trisulfonic acid) and extraction of the rhodium complex Starting materials

| | |
|---|---|
| (a) TPPTS/Rh solution, spent | 100 g |
| toluene (extraction agent) | 100 g |
| 2-ethylhexanol (solubiliser) | 30 g |
| di-(n-pentyl)-amine (mol. wt. 157.3) | 18.5 g |
| sulfuric acid 10% | 85 g |
| (amine/TPPTS + TPPDS 1.75 Mol/equiv.) | |
| toluene | 80 g |
| 2-ethylhexanol | 20 g |
| deionized water | 500 g |
| (b) sodium hydroxide, 1 N | 80 g |
| sulfuric acid, concentrated | 1.3 g |

Results

| | TPPTS/Rh-solution, spent 100 g | TPPTS-solution from pre-cipitation 117 g | filtrate: toluene phase 204 g | filtrate: aqueous phase 639 g |
|---|---|---|---|---|
| TPPTS g | 12.68 | 9.01 | 1.99 | 0.21 |
| TPPOTS g | 5.12 | 0.38 | 0.60 | 5.35 |
| TPPSTS g | 0.52 | 0.16 | 0.26 | 0.10 |
| TPPDS g | 0.07 | 0.04 | 0.02 | |
| TPPODS g | 1.47 | | 0.43 | 1.08 |
| TPPSDS g | 0.02 | | 0.01 | |
| BSNS g | 0.69 | | 0.12 | 0.53 |
| other components | 2.79 | 0.04 | 0.41 | 2.0 |

TABLE IV-continued

| Rh % | 100 | 1.9 | 81.8 | 16.3 |
|---|---|---|---|---|

Various modifications of the process of the invention may be made without departing from the spirit or scope thereof and it should be understood that the invention is intended to be limited only as defined in the appended claims.

We claim:

1. A process for the purification of salts of at least one member of the group consisting of diphenylphosphine-phenyl-m-sulfonic acid, phenylphosphine-di-(m-phenyl-sulfonic acid) and triphenylphosphine-tri-(m-sulfonic acid) from aqueous solutions thereof comprising adding at least a molar equivalent amount of at least one member of the group consisting of di-(n-pentyl)-amine, di-(n-hexyl)-amine and water-soluble salts of said amines to an aqueous solution containing at least one member of the group consisting of diphenylphosphine-phenyl-m-sulfonic acid, phenylphosphine-di-(m-phenylsulfonic acid), triphenylphosphine-tri(m-sulfonic acid) and salts thereof to adjust the pH value to $\leq 7$, recovering the precipitate, washing the precipitate and dissolving the same in an aqueous basic solution.

2. The process of claim 1 wherein the amount of amine used is 1.0 to 1.5 equivalents based on the sulfonic acid.

3. The process of claim 1 wherein the concentration of the said sulfonic acid is 2 to 15% by weight based on the solution.

4. The process of claim 1 wherein the temperature during the amine is $-10°$ to $10°$ C.

5. The process of claim 1 wherein the precipitate was washed with water and optionally with an aliphatic or aromatic hydrocarbon.

6. The process of claim 1 wherein the aqueous solution of the sulfonic acid to which the amine component is added is obtained from the sulfonation of triphenylphosphine with oleum followed by water dilution.

7. The process of claim 1 wherein the aqueous solution of the sulfonic acid to which the amine component is added contains a metal catalyst.

* * * * *